US006941819B1

United States Patent
Maki, Jr. et al.

(10) Patent No.: US 6,941,819 B1
(45) Date of Patent: Sep. 13, 2005

(54) APPARATUS AND METHOD FOR DETERMINING THE DYNAMIC MECHANICAL PROPERTIES OF A CEMENT SAMPLE

(75) Inventors: Voldi E. Maki, Jr., Austin, TX (US); Steven L. Cobb, Tulsa, OK (US)

(73) Assignee: Chandler Instruments Company L.L.C., Houston, TX (US)

( * ) Notice: Subject to any disclaimer, the term of this patent is extended or adjusted under 35 U.S.C. 154(b) by 0 days.

(21) Appl. No.: 10/260,707

(22) Filed: Sep. 30, 2002

Related U.S. Application Data

(60) Provisional application No. 60/325,611, filed on Sep. 28, 2001.

(51) Int. Cl.[7] .............................................. G01N 3/00
(52) U.S. Cl. ........................................ 73/803; 73/788
(58) Field of Search ......................... 73/788–803, 804, 73/594, 865.5

(56) References Cited

U.S. PATENT DOCUMENTS

| | | | |
|---|---|---|---|
| 2,833,142 A | 5/1958 | Runquist et al. ............... 73/53 |
| 3,641,811 A | 2/1972 | Gnaedinger, Jr. et al. ....... 73/69 |
| 4,073,193 A * | 2/1978 | Mastandrea ................ 73/865.5 |
| 4,254,479 A * | 3/1981 | Wiley .......................... 367/35 |
| 4,259,868 A | 4/1981 | Rao et al. ..................... 73/597 |
| 4,265,120 A | 5/1981 | Morris et al. ................. 73/600 |
| 4,377,087 A | 3/1983 | Rodot ......................... 73/594 |
| 4,380,930 A * | 4/1983 | Podhrasky et al. ........... 73/594 |
| 4,567,765 A | 2/1986 | Rao et al. ..................... 73/594 |
| 4,622,846 A | 11/1986 | Moon, Jr. et al. ............... 73/59 |
| 4,625,542 A * | 12/1986 | Nelson ........................ 73/1.83 |
| 4,649,750 A | 3/1987 | Cantrell, Jr. et al. .......... 73/599 |
| 4,655,084 A | 4/1987 | Renzel ........................ 73/611 |
| 4,754,645 A | 7/1988 | Piche et al. ................... 73/597 |
| 4,843,598 A * | 6/1989 | Medlin ......................... 367/27 |
| 4,862,384 A | 8/1989 | Bujard et al. ................ 364/509 |
| 5,001,676 A * | 3/1991 | Broding ....................... 367/31 |
| 5,009,102 A | 4/1991 | Afromowitz ................. 73/590 |
| 5,089,989 A * | 2/1992 | Schmidt et al. ............... 367/35 |
| 5,092,176 A | 3/1992 | Buttram et al. ............... 73/599 |
| 5,099,849 A | 3/1992 | Rossman et al. ....... 128/661.03 |
| 5,119,820 A | 6/1992 | Rossman et al. ....... 128/661.03 |
| 5,412,990 A | 5/1995 | D'Angelo et al. ............ 73/597 |
| 5,433,112 A | 7/1995 | Piche et al. ................... 73/597 |
| 5,625,140 A * | 4/1997 | Cadet et al. ............... 73/24.01 |

(Continued)

FOREIGN PATENT DOCUMENTS

| | | | |
|---|---|---|---|
| DE | 196 26 111 C1 | 10/1997 | .......... G01N 17/00 |

(Continued)

*Primary Examiner*—Max Noori
*Assistant Examiner*—Alandra Ellington
(74) *Attorney, Agent, or Firm*—Fellers, Snider, Blankenship, Bailey & Tippens, P.C.

(57) ABSTRACT

An apparatus for determining dynamic mechanical properties of a cement sample. The apparatus includes an isolator located within a cavity defined by a body. The isolator has an attached end that engages the body proximate a narrow end of the cavity. A space between the body and isolator facilitates lateral movement the isolator. A transducer is located in an interior space defined by the isolator. The transducer has an attached end engaging a distal end of the isolator. A space between the isolator and transducer facilitates lateral movement of the transducer distal end. The transducer generates compressional waves and shear waves that travel into the sample. An ultrasonic receiver receives the waves. The waves are separated with filtering. Sample setting time may be determined from propagation time of shear waves through the sample. Compressive strength of the sample is determined by velocity of compressional waves as the sample sets.

16 Claims, 2 Drawing Sheets

U.S. PATENT DOCUMENTS

| | | | |
|---|---|---|---|
| 5,741,971 A | 4/1998 | Lacy | 73/597 |
| 5,763,773 A * | 6/1998 | Birchak et al. | 73/152.58 |
| 5,846,462 A | 12/1998 | Thompson | 264/51 |
| 5,853,475 A | 12/1998 | Liskowitz et al. | 106/705 |
| 5,992,223 A | 11/1999 | Sabins et al. | 73/64.42 |
| 6,070,465 A * | 6/2000 | Maki, Jr. | 73/594 |
| 6,112,599 A * | 9/2000 | Maki, Jr. | 73/801 |
| 6,345,535 B1 | 2/2002 | Sabins et al. | 73/818 |
| 6,483,777 B1 * | 11/2002 | Zeroug | 367/35 |

FOREIGN PATENT DOCUMENTS

| | | | |
|---|---|---|---|
| EP | 0 577 511 A1 | 1/1994 | G01N 29/02 |

\* cited by examiner

APPARATUS AND METHOD FOR DETERMINING THE DYNAMIC MECHANICAL PROPERTIES OF A CEMENT SAMPLE

CROSS REFERENCE TO RELATED APPLICATION

This application claims the benefit of U.S. Provisional Application No. 60/325,611, which application was filed with the Patent and Trademark Office on Sep. 28, 2001.

BACKGROUND OF THE INVENTION

1. Field of the Invention

The present invention relates to a transducer for simultaneously producing compressional and shear waves in a cement sample. More particularly, but not by way of limitation, the present invention relates to a transducer which allows the measurement of the shear wave velocity and compressional wave velocity in a universal cement analyzer cell so as to determine dynamic mechanical properties, i.e., Poisson's ratio and Young's modulus, as well as other properties of a cement sample.

2. Background of the Invention

Ultrasonic cement analyzers ("UCA") are well known in the art. Compressive strength measurements of a cement sample are best taken using such a device. While the UCA provides a number of advantages over alternative methods for measuring, or estimating, the characteristics of a particular cement sample, a compelling advantage is the ability of the UCA to perform nondestructive measurements. Thus, a single sample may be used to perform a series of measurements, whereas, with alternative methods, a series of samples are required for each measurement to be made. Using a single sample reduces cost, provides more consistent testing, reduces record keeping, saves time, etc.

The UCA was developed to measure the compressive strength of a cement slurry as it sets when subjected to simulated oil field temperatures and pressures. It consists of a high temperature-high pressure autoclave, a heat jacket capable of heating rates up to 5.6.degree. C. (10.degree. F.) per minute, a pair of 400 kHz ultrasonic transducers for measuring the transit time of an acoustic signal transmitted through the slurry, plus associated hydraulic plumbing. The two transducers make transit time measurements through the cement as it sets. A short pulse on a lower transducer propagates through the cement to an upper transducer. Set time and compressive strength are calculated from measured transit time via empirically developed equations. U.S. Pat. Nos. 4,259,868 and 4,567,765 disclose the UCA in detail and are incorporated herein by reference.

It is also known in the art that an acoustic shear wave may be used to determine the setting time of cement. In one method for using a shear wave to determine setting time, a shear wave is generated at a location in a cement slurry. The point in time at which the shear wave propagates through the slurry is indicative of the setting time of the cement. U.S. Pat. No. 5,412,990 issued to D'Angelo et al. discloses such a method for measuring cement thickening time using a shear wave and is hereby incorporated by reference.

In addition, if both the shear wave velocity and compressional wave velocity are known, it is possible to calculate various dynamic mechanical properties of the sample such as Poisson's ratio, Young's modulus, etc. Poisson's ratio is defined as the absolute value of the ratio of transverse strain to the corresponding axial strain resulting from uniformly distributed axial stress below the proportional limit of the material. Young's modulus is the elastic modulus in tension or compression. This information if useful for material development or characterization as well as for quality control purposes. While wave velocities have been employed for the measurement of dynamic mechanical properties in rock specimens, they have not heretofore been used to determine such properties in a cement sample.

An additional disadvantage associated with traditional UCA devices is that, historically, all acoustic cement tests have been run with the cell oriented vertically. With some cement samples, a layer of low strength material forms at the top, which can cause a limitation in the transfer of acoustic energy from the cell/transducer, to the cement at the send end. Further, the low strength material can cause a limitation in the transfer of acoustic energy from the cement to the cell/transducer at the receiving end.

It is thus an object of the present invention to provide a transducer which may be used to simultaneously produce shear and compressional waves in a cement sample.

It is yet a further object of the present invention to provide an ultrasonic cement analyzer which will measure shear wave and compressional wave velocities.

It is still a further object of the present invention to provide a method for measuring the velocities of the shear and compressional waves produced in a sample and to indicate the dynamic mechanical properties of the sample.

It is a further object of the present invention to provide an apparatus and method for overcoming limitations in a transfer of acoustic energy from the cell/transducer to the cement and vise versa due to low strength material adjacent the transducer.

SUMMARY OF THE INVENTION

The present invention provides a transducer which will simultaneously produce shear and compressional waves in a sample and a method for using the measured velocities of the shear and compressional waves to determine dynamic mechanical properties of the sample such as Poisson's ratio.

In a preferred embodiment, an ultrasonic transducer is mounted in an end plug for a standard UCA cell. The transducer is in acoustic communication with an acoustic element mounted in an isolator such that acoustic element is free to move laterally for production of the shear wave. When an electrical pulse is applied to the transducer, an acoustic pulse travels axially down the acoustic element and into the cement sample as a compressional wave. In addition, the acoustic element moves laterally in response to the electrical pulse to also produce a shear wave in the sample. The internal portion of the inventive acoustic element is secured to the isolator at the end furthest from the cement sample thereby allowing greater freedom of movement in the lateral direction than has heretofore been possible.

In another embodiment, the velocities of the compressional wave and shear wave produced by the inventive transducer are measured to determine the dynamic mechanical properties, for example Poisson's ratio and Young's modulus, of the sample under test.

In addition, the UCA may also provide all of the features and perform all of the functions of a conventional UCA. Thus, an UCA incorporating the present invention provides a convenient method to measure the change in mechanical properties of a cement sample at elevated temperatures and pressures as the sample transitions from a slurry, through gelation, to a solid, as setting occurs.

In one embodiment, the transmission and reception of acoustic energy is improved by orienting the transducers and sample in a horizontal configuration. In a horizontal orientation, the cement sample in contact with the centralized transducer is an average of the cement in the cell. If a weak "punky" layer of cement then forms at or near the top of the cement sample, the weak layer will be adjacent a wall of the sample cylinder rather than adjacent a transducer.

Other benefits of a horizontal orientation are observable when testing "foamed" cements that have a meaningful percentage of entrained gas, e.g., 10% to 40% entrained gas, although other percentages are also contemplated to be used with the invention. As the cement is pressurized, the gas bubble become smaller. Therefore, a gap can form between the cement and the cell/transducer. The gap can be large enough that tests cannot be run. However, when placed in a horizontal orientation, the cement sample volume can change substantially before the acoustic analysis is seriously affected.

In another embodiment, the transmission and reception of acoustic energy is improved by forcing the transducer into contact with the sample with a piston or other force applying device.

Further objects, features, and advantages of the present invention will be apparent to those skilled in the art upon examining the accompanying drawings and upon reading the following description of the preferred embodiments.

DESCRIPTION OF THE PREFERRED EMBODIMENTS

Before explaining the present invention in detail, it is important to understand that the invention is not limited in its application to the details of the construction illustrated and the steps described herein. The invention is capable of other embodiments and of being practiced or carried out in a variety of ways. It is to be understood that the phraseology and terminology employed herein is for the purpose of description and not of limitation.

Figure 1:
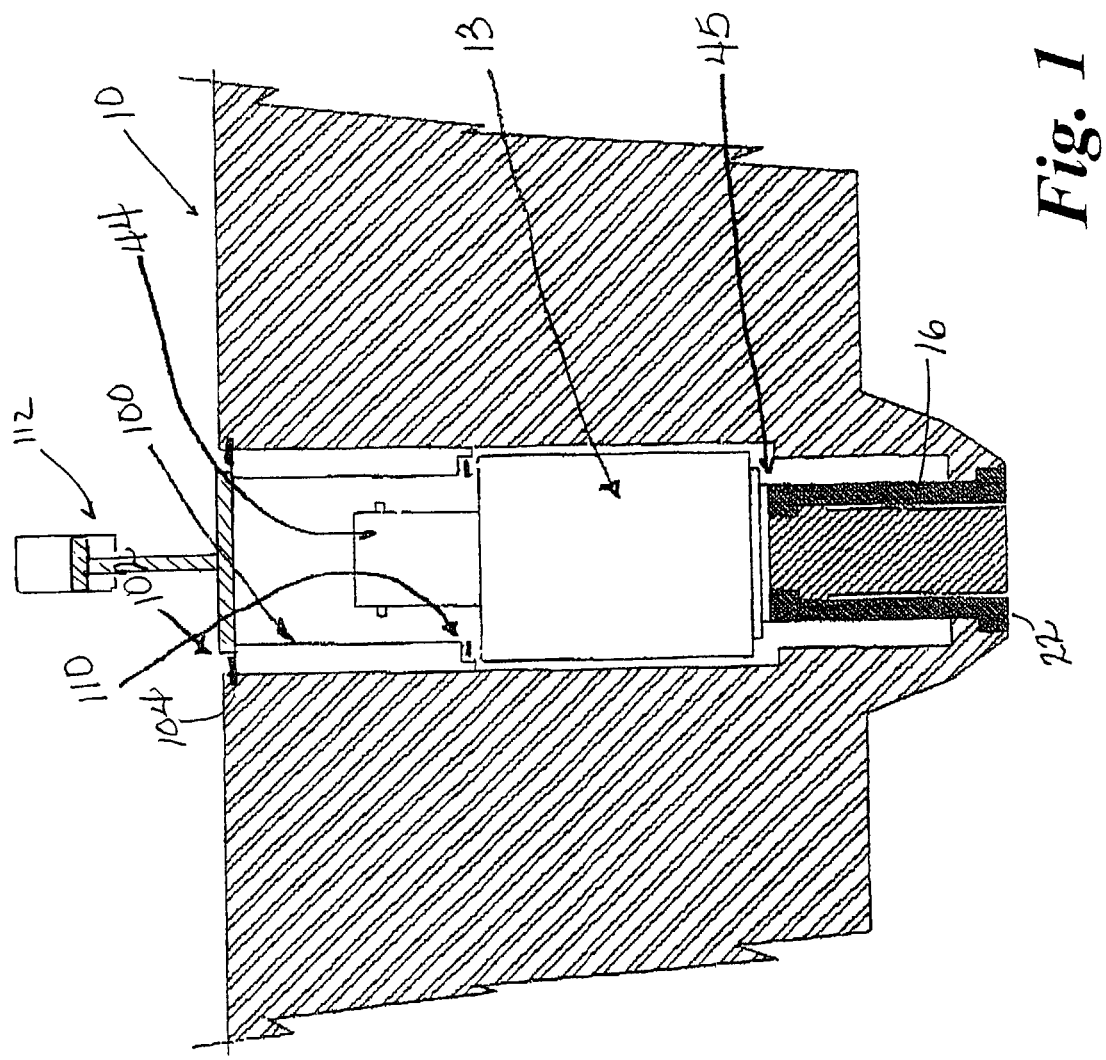
FIG. 1 provides a cross-sectional side view of an end plug for an ultrasonic cement analyzer having the inventive transducer mounted therein.

A typical end plug 10 for an ultrasonic cement analyzer ("UCA") is shown in FIG. 1. Preferably, end plug 10 has transducer 12 mounted therein such that a contacting surface 14 of transducer 12 can contact a cement sample contained in a UCA cell (not shown) to be capped with end plug 10. It should be noted that surface 14 may protrude slightly below bottom surface 60 and end 22 to improve contact with the sample.

Preferably, transducer 12 includes: transmitter 13, body 38, and acoustic couplant 45. Delay line 15 includes isolator 16; and acoustic element 18. Isolator 16 is essentially cylindrical in appearance having: flange 20 extending radially outward from end 22; an exterior side wall 24 extending upward from flange 20 to distal end 26; cylindrical cavity 28 formed by interior wall 30; and top wall 32 having aperture 34 opening into cavity 28.

Ultrasonic transmitter 13 is preferably a commercially available transducer. One such ultrasonic transducer is the Harisonic transducer used with prior art UCA devices. Preferably transmitter 13 includes: a body 42 and an electrical connector 44 for receiving electrical pulses to excite transmitter 13. Preferably connector 44 is a BNC-type connector.

Figure 2:
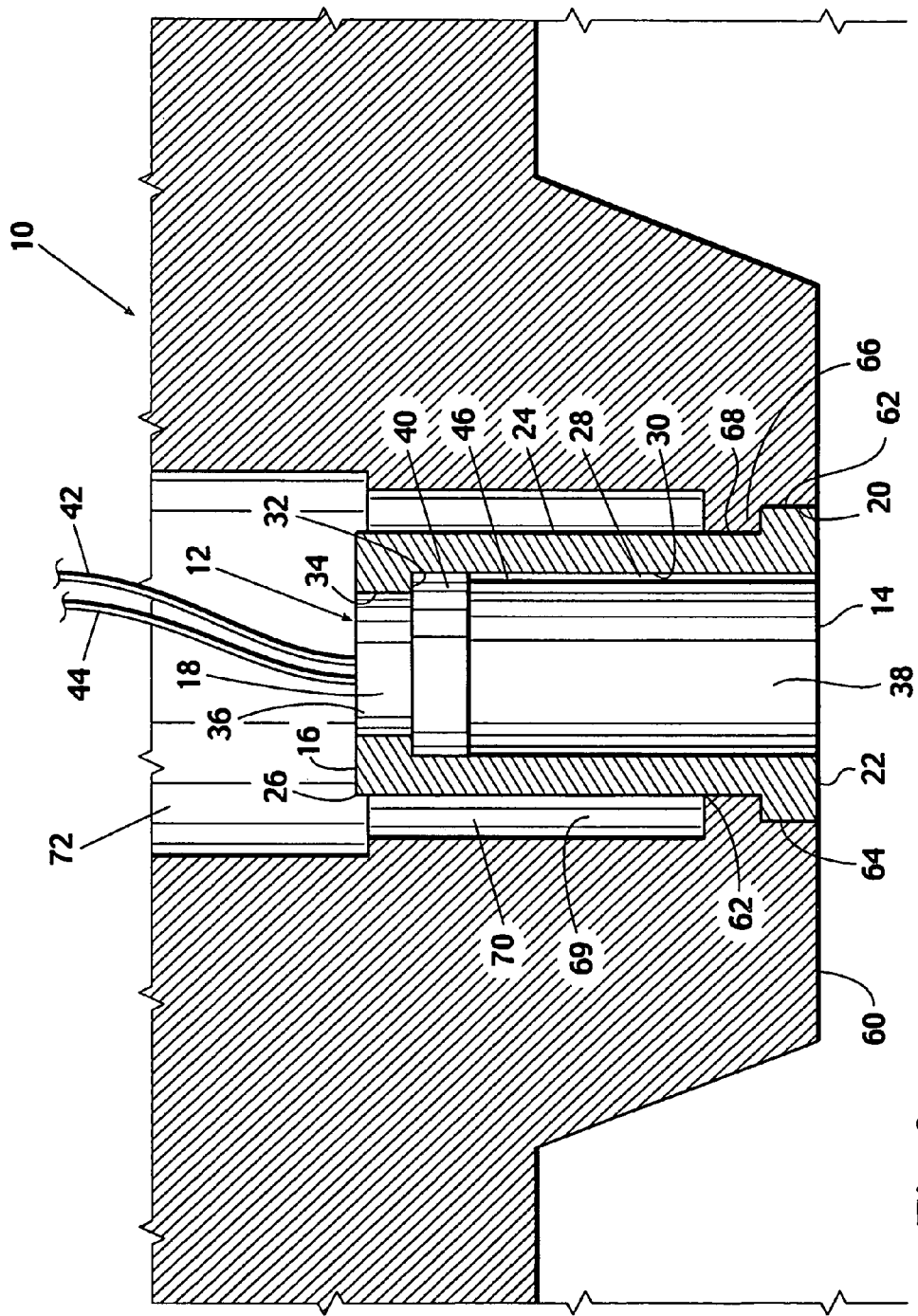
FIG. 2 provides a cross-sectional side view of an end plug for the ultrasonic cement analyzer having the inventive shear wave transducer mounted therein showing the acoustic element and isolator in greater detail.

Referring now to FIGS. 1 and 2, acoustic element 18 is typically a unitary structure formed from metal, or other rigid material, and includes: a cylindrical top end 36; a cylindrical body portion 38; a flange 40 separating end 36 from body 38.

Transducer 12 is assembled by pressing top end 36 in to aperture 34 until flange 40 contacts top wall 32. Most preferably, cavity 28 has a diameter somewhat larger than the diameter of body 38 so that a gap 46 is formed between body portion 38 and interior wall 30. Acoustic energy is coupled from transmitter 13 to acoustic element 18 through acoustic couplant 45.

Preferably, end plug 10 includes a bottom surface 60 having cavity 62 therein. Cavity 62 is generally a series of coaxial cylindrical cavities of varying diameter giving cavity 62 a "stepped" appearance. In a preferred embodiment, cavity 62 has a lower cylindrical cavity 64 which is preferably sized to receive flange 20 of isolator 16. Flange 66 is defined by a second cylindrical cavity 68 having a smaller diameter than that of cavity 64. Above flange 66, a third cavity 69 is formed of a larger diameter than that of body 38 creating a cylindrical gap 70 and, finally, an upper cavity 72 is formed, preferably extending to the top surface (not shown) of end plug 10.

When transducer 12 is installed in end plug 10, housing 16 is inserted into cavity 62 until flange 20 contacts flange 66. Transmitter 13 is placed above body 38 and held in place with sleeve 100 and snap ring 102 placed in snap ring groove 104 near the upper end of cavity 72. Wave spring 110 maintains pressure between transmitter 13 and acoustic couplant 45 and body 38. As will be apparent to those skilled in the art, body 38 is thus only supported at its lower end. When a pulse is applied to transmitter 13, acoustic element 18 is driven in its axial direction which will generate a compressional wave in a cement sample in contact with end 14. In addition, an electrical pulse applied to transmitter 13 will also result in lateral movement of acoustic element 18. In prior art designs, transmitter 13 was pressed directly into end plug 10 at surface 60. The mass of end plug 10 and the rigid mounting of transmitter 13 near the sample greatly limited the generation of a shear wave in the sample. In contrast, in the inventive transducer, the mass of the end plug 10 is, to a large degree, isolated from transducer 12 since isolator 16 is secured at its lower end and acoustic element 18 is secured at its upper end. Gaps 46 and 70 reduce the degree to which end plug 10 attenuates lateral movement of acoustic element 18. Thus, the amplitude of the shear wave produced by the inventive transducer 12 will be many times greater than would be produced if transmitter 13 were simply mounted directly in end plug 10.

To further improve the transmission and reception of acoustic energy, the transducer may be forced into contact with the sample by a piston 112 (FIG. 1). As shown in FIG. 1, piston 112 acts on the sleeve 100 to compress the wave spring 110, and force transmitter 13, isolator 16, and transducer 12 to move so that transducer 12 is forced into contact with a sample. Although piston 112 is shown in FIG. 1 as an example, other force applying devices may be used. Further piston 112 may be located elsewhere to impart force to transducer 12. For example, piston 112 may be keyed to end plug 10 and act directly on isolator 16 or may be configured in other ways.

As will be apparent to those skilled in the art, to determine the velocities of the compressional wave and shear wave independently, there must be some method for distinguishing each wave independently at a receiver. Two techniques are possible with the inventive apparatus.

First, in a typical sample, the shear wave will arrive at a receiver later than the compressional wave. Thus, a time based method may be used to distinguish between the two waves. Those familiar with cement analyzers will appreciate that, typically, a second end plug, capping the opposite end of the UCA cell, may be configured to house an ultrasonic receiver. After the generation of the waves in the sample, the first ultrasonic pulse received will indicate the arrival of the compressional wave. The velocity of the wave may simply be calculated by dividing the distance between the receiver and transmitter by the elapsed time between transmittal of the pulse and its arrival at the receiver. The second ultrasonic pulse received will be as a result of the shear wave. The shear wave velocity is likewise calculated by dividing the distance between the transmitter and receiver by the time period between excitation of the transmitter and the and receipt of the second pulse.

Alternatively, it is also possible to generate the shear wave at a frequency different from that of the compressional wave which allows the two waves to be measured independently through filtering of the received signal. Since the shear wave velocity in steel is typically half the speed of the compressional wave velocity, the shear wave frequency generated by the inventive transducer 12 will be approximately half the frequency of the compressional wave. As will be apparent to those skilled in the art, after the compressional and shear wave are received, the two waves may be separated with relatively simple electrical filtering.

The importance in measuring the velocities of the shear wave and compressional wave is that, when such values are known, it is possible to calculate dynamic mechanical properties of the sample such as, for example, Poisson's ratio and Young's modulus. As will be apparent to those skilled in the art, known relationships have been demonstrated between the compressional and shear wave velocities and various mechanical properties of specific materials.

For example, it has previously been shown that Poisson's ratio and Young's modulus for a rock specimen may be determined if the acoustical compressional and shear wave velocities are known for that specimen. In such a specimen, Young's modulus (E) is given by:

$$E = C_S^2 \rho [3(C_P/C_S)^2 - 4]/(C_P/C_S)^2 - 1]$$

where:
   $C_S$ is the velocity of the shear wave through the specimen;
   $C_P$ is the velocity of the compressional wave through the specimen; and
   $\rho$ is the density of the material.

Poisson's ratio ($\mu$) is given by:

$$\mu = \frac{1}{2}[(C_P/C_S)^2 - 2]/[(C_P/C_S)^2 - 1]$$

As will be apparent to those skilled in the art, the above equations may vary somewhat depending on the particular geometry of the specimen measured, however it is within the skill level of one of ordinary skill in the art to empirically determine such modifications. Likewise, while these equations would provide a good estimate for Young's modulus and Poisson's ratio for a cement sample tested in a UCA, modifying the equations to account for the particular geometry of the UCA test cell and differences between a rock specimen and a cement specimen could improve the accuracy of the calculation. Again, it is within the skill level of one of ordinary skill in the art to empirically determine such modifications.

It should thus be noted that, when using an UCA employing a shear transducer, such as the inventive shear transducer, a cement sample may be tested at elevated pressures and temperatures which actually simulate those encountered in casing an oil or gas well. In addition, as an individual sample sets, it is possible to determine a number of mechanical properties of the sample as the cement transitions from a slurry, through the gelation stage, and into a solid. As discussed above, the setting time may be determined from the point in time at which a shear wave will propagate through the sample, the compressive strength may be determined from the velocity of the compressional wave as the cement sets, and the dynamic mechanical properties (i.e., Poisson's ratio and Young's modulus) may be determined from the velocities of the shear and compressional waves as the cement transitions into the solid state. In such a UCA, it is possible to measure, display, and record changes in the mechanical properties of the sample as setting occurs.

In an additional embodiment of the invention, further improvement to the UCA process can be achieved by orienting the transducer, receiver and sample horizontally rather than vertically.

Thus, the present invention is well adapted to carry out the objects and attain the ends and advantages mentioned above as well as those inherent therein. While presently preferred embodiments have been described for purposes of this disclosure, numerous changes and modifications will be apparent to those skilled in the art. Such changes and modifications are encompassed within the spirit of this invention.

What is claimed is:

1. An apparatus for determining the dynamic mechanical properties of a cement sample comprising:
   an end plug adapted for use with an ultrasonic cement analyzer;
   a horizontally mounted transducer within a cavity in said end plug, said transducer having an attached end and a free end;
   wherein said transducer is supported on only said attached end, thereby permitting said free end to move laterally for generating a shear wave.

2. An apparatus for determining the dynamic mechanical properties of a cement sample comprising:
   a body defining a cavity, said cavity having a wide end and a narrow end;
   an isolator within said cavity, said isolator having an attached end and a distal end and having an internal wall that defines an interior space, said attached end engaging said body proximate said narrow end of said cavity;
   a transducer having an attached end and a free end, said transducer in said interior space of said isolator, said attached end of said transducer engaging said isolator proximate said distal end of said isolator; and
   wherein said transducer is capable of generating a compressive wave that travels into the sample and said transducer is also capable of generating a shear wave that travels into the sample.

3. The apparatus according to claim 2 wherein:
   said cavity of said body and an exterior wall of said isolator define a space therebetween, said space for facilitating lateral movement of said distal end of said isolator.

4. The apparatus according to claim 2 wherein:
said internal wall of said isolator and a body portion of said transducer define a space therebetween, said space for facilitating lateral movement of said distal end of said transducer.

5. The apparatus according to claim 2 further comprising:
an ultrasonic receiver housed in a second body at an opposite end of the sample for receiving said compressive wave and said shear wave.

6. The apparatus according to claim 2 wherein:
said body, isolator and transducer are oriented vertically.

7. The apparatus according to claim 2 further comprising:
a force applicator in communication with said transducer, for forcing said transducer into contact with the sample.

8. The apparatus according to claim 1 further comprising:
a transmitter having a first end and a second end, said second end in communication with said distal end of said isolator.

9. The apparatus according to claim 8 further comprising:
an acoustic couplant having a first end and a second end, said first end in communication with said second end of said transmitter, said second end of said acoustic couplant in communication with said distal end of said isolator.

10. The apparatus according to claim 9 further comprising:
a sleeve in said cavity of said body, said sleeve having a contacting end;
a wave spring having a first side and a second side, said first side in communication with said contacting end of said sleeve and said second side in communication with said first end of said transmitter; and
wherein said wave spring maintains pressure between said transmitter and said acoustic couplant.

11. A method for determining dynamic mechanical properties of a cement sample comprising the steps of:
generating a compressive wave and a shear wave with a transducer;
propagating said compressive wave and said shear wave into the sample;
receiving said compressive wave and said shear wave with an ultrasonic receiver; and
separating said compressive wave and said shear wave with electrical filtering.

12. The method according to claim 11 further comprising the step of:
determining setting time of the sample from a point in time at which said shear wave will propagate through the sample.

13. The method according to claim 11 further comprising the step of:
determining compressive strength of the sample from velocity of the compressive wave as the sample sets.

14. The method according to claim 11 wherein:
dynamic mechanical properties may be determined from velocities of said shear wave and said compressive wave as the sample transitions into a solid state.

15. The method according to claim 11 wherein:
said step of propagating is conducted as the sample is in a state selected from a group consisting of a slurry, a gelation stage, a solid, a transition from a slurry to a gelation phase and a transition from a gelation stage into a solid.

16. The method according to claim 11 further comprising the step of:
forcing said transducer into contact with the sample.

* * * * *

UNITED STATES PATENT AND TRADEMARK OFFICE
CERTIFICATE OF CORRECTION

PATENT NO. : 6,941,819 B1
DATED : September 13, 2005
INVENTOR(S) : Voldi E. Maki, Jr. et al.

It is certified that error appears in the above-identified patent and that said Letters Patent is hereby corrected as shown below:

Column 7,
Line 15, should read -- 8. The apparatus according to claim 2 further comprising: --.

Signed and Sealed this

Twenty-ninth Day of November, 2005

JON W. DUDAS
*Director of the United States Patent and Trademark Office*